United States Patent
Ishizawa et al.

(10) Patent No.: US 6,890,761 B2
(45) Date of Patent: May 10, 2005

(54) AUTOMATIC ANALYZER

(75) Inventors: Masato Ishizawa, Hitachinaka (JP); Hideyuki Yanami, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 602 days.

(21) Appl. No.: 09/940,592

(22) Filed: Aug. 29, 2001

(65) Prior Publication Data

US 2002/0064481 A1 May 30, 2002

(30) Foreign Application Priority Data

Nov. 28, 2000 (JP) ........................................ 2000-365763

(51) Int. Cl.[7] .................................................. B01L 3/02
(52) U.S. Cl. ........................... 436/180; 422/64; 422/67; 422/100; 73/864.24; 436/50
(58) Field of Search .................. 436/50, 180; 422/100, 422/63–67; 73/864.24, 864.25

(56) References Cited

U.S. PATENT DOCUMENTS

2002/0110493 A1 * 8/2002 Dales et al. ................. 422/100

FOREIGN PATENT DOCUMENTS

| JP | 6-123743 | 6/1994 |
|----|----------|--------|
| JP | 08-285661 | 11/1996 |
| JP | 11-271322 | 10/1999 |
| JP | 11-271328 | 10/1999 |
| JP | 11-352132 | 12/1999 |
| JP | 2000-171470 | 6/2000 |
| JP | 2000-221201 | 8/2000 |

OTHER PUBLICATIONS

Machine translation, JP 08–285661 (Nov. 1, 1996).*
Machine translation, JP 2000–171470 (Jun. 23, 2000).*

* cited by examiner

Primary Examiner—Jan M. Ludlow
(74) Attorney, Agent, or Firm—Mattingly, Stanger & Malur, P.C.

(57) ABSTRACT

In order to reduce carry-over of sample liquids in an automatic analyzer by a pipeting probe and resulting contamination of sample liquids by immersing the pipeting probe into sample liquids as shallow as possible, said pipeting probe is moving down to a position which is calculated and determined according to the detected height of a container temporarily stopping said probe there, and further moving down said probe to immerse said probe into the liquid in said container.

6 Claims, 5 Drawing Sheets

AUTOMATIC ANALYZER

BACKGROUND OF THE INVENTION

The present invention relates to an analyzer for analyzing biomaterial such as blood or urine, particularly to an automatic analyzer equipped with a function of pipeting liquid from one container to another container by means of a pipetting probe.

To analyze the component of a sample containing biomaterial such as blood or urine, reagent is mixed in the sample and the color of the reaction liquid is measured by a measuring means such as a photometer. There has been available an automatic analyzer automating all these analysis processes, including pouring (pipeting) the sample from a sample container into a reaction container on a reaction line, mixing the reagent, measuring a mixture of the sample and reagent by a photometer, and outputting the analysis result.

To pipet the sample, the tip of a pipetting probe is dipped into the liquid for pipetting inside a sample container and the liquid is sucked by a pump or similar means, and then the sucked liquid is discharged into a reaction container. In this process, if the dipping depth of the probe into the liquid is greater, the amount of liquid adhering to the outside wall of the probe increases. The liquid adhering on the outside wall of the probe, which may be mixed into another sample to be analyzed next in the course of pipeting the sample, can be a cause of increasing so-called contamination. In order to reduce the dipping depth of the tip of the pipetting probe into the sample liquid as much as possible, the motion of the pipetting probe is so controlled that the liquid surface of the liquid inside the container is detected, the descending motion of the probe is stopped when the tip of the probe reaches a position slightly below the liquid surface, and then a specified amount of the liquid is sucked into the probe.

Known methods of detecting the liquid surface include a method by means of detecting a change in the capacitance or resistance of the sample, a method by means of detecting a change in the refraction or reflection of light or ultrasonic wave, and a method by means of detecting a change in the pressure inside the pipetting probe. Brief steps of measuring the liquid surface by a change in the capacitance are as follows. The pipetting probes and sample containers, or sample holders, are made of conductive material and the capacitance through the sample is measured. First, the capacitance at the upper dead point of the probe is registered in memory as a reference. Then, an increase in the capacitance at the time when the pipetting probe descends and contacts the liquid surface is detected and the liquid surface is judged to be detected, using the increase in the capacitance as a trigger. Disclosed in U.S. Pat. No. 5,049,826 is a prior art using the afore-mentioned upper dead point as a reference.

Problems to be Solved by the Invention

In an automatic analyzer according to the above prior art, a number of sample containers containing the sample to be analyzed are placed on a sample disk or rack, which is a mode of holding the containers. Several types of sample containers with different sizes are frequently used and the containers, particularly small sample containers are sometimes set directly on a sample disk or rack but sometimes set indirectly as they are set on other containers or auxiliary holders placed on the sample setting position of the sample disc or rack.

In the liquid surface detection using the upper dead point as a reference, the moving distance of the pipetting probe from the liquid surface detection start position to the liquid surface position naturally differs by the size of the sample container. Although the dipping depth of the tip of the pipetting probe must be reduced as much as possible in view of the analyzing performance, the pipetting probe needs to be descended always in preparation for an immediate halt at any position after the liquid surface detection start position because the position of the liquid surface is not known as explained above. However, in case a disturbance noise is caused in the course of the liquid surface detection, that is, to be concrete, in case that the static electricity charged in the sample container is discharged towards the pipetting probe, for example, the liquid surface detecting means wrongly detects the liquid surface due to the noise caused as above and consequently the liquid surface detection is not accomplished completely. To avoid wrong detection, a noise allowance is given for the judgment of the liquid surface. If the allowable time (allowance) is set longer, a noise of wider band can be neglected and hence the resistance against noise improves. On the other hand, in detecting the liquid surface actually, the above means that the probe does not stops but dips further into the sample even when the probe has contacted the liquid surface. This event increases the dipping depth and may give adverse effect on the analyzing performance. Generally, in the prior art, the noise allowance is set to the minimum so as to reduce the dipping depth as much as possible. This method, however, does not allow to detect the liquid surface due to the effect of noise, resulting in abnormal pipetting.

SUMMARY OF THE INVENTION

An object of the present invention is to provide an automatic analyzer eliminating the effect of noise and being capable of detecting the liquid surface correctly.

In order to achieve the above object, according to the present invention, there is provided an automatic analyzer comprising a means for descending a pipetting probe so that the pipetting probe can be dipped in the liquid in a first container, a means for pipeting the liquid inside the first container into a second container by means of the pipetting probe, and a means for measuring the content inside the second container; wherein: there is provided a means for detecting the height of the first container; the pipetting probe is descended to a preset position calculated on the basis of the detection result of the detecting means; then the pipetting probe is halted; and then the pipetting probe is further descended so that the pipetting probe is dipped in the liquid inside the first container.

DETAILED DESCRIPTION OF THE PREFERRED EMBODIMENT

Preferred embodiments of the present invention are explained below, using FIG. 1 to FIG. 9.

FIG. 1 is a schematic diagram of the pipetting mechanism and peripherals of an automatic analyzer to which the present invention applies. Analysis procedures are as follows. The sampling arm 2 of a sampling mechanism 1 is designed to move vertically and swing horizontally so as to suck the sample 7 from a sample container 101, placed on a sample disk 102 designed to rotate horizontally, and discharge it into a reaction container 106, using a probe 105 mounted on the sampling arm 2. Generally, as known from this figure, the sample disk 102 is designed for universal placement of the sample containers 101 so as to be able to place the sample containers 101 directly on the sample disk 102 or over test tubes (not shown). A test tube is normally 50 mm to 100 mm long approximately.

The construction of the automatic analyzer in FIG. 1 is explained in more detail. Reagent bottles 112, each corresponding to a different item of analysis, are placed on a reagent disk 125 designed to rotate freely. A reagent pipetting probe 110 mounted on a movable arm pipets a specified amount of reagent from the reagent bottles 112 into the reaction container 106.

The sample pipetting probe 105 sucks and discharges the sample in accordance with the operation of a syringe pump 107 for sample. The reagent pipetting probe 110 sucks and discharges the reagent in accordance with the operation of a syringe pump 111 for reagent. Items of analysis of each sample are inputted from an input device such as from a keyboard 121 or from the screen of a CRT 118. The operation of each unit of the automatic analyzer is controlled by a computer 103.

A sample container 101 is moved to a sample sucking position in accordance with the intermittent rotation of the sample disk 102 and the sample pipetting probe 105 descends into the sample container at a halt. In the course of the descending motion, as soon as the tip of the pipetting probe 105 contacts the liquid surface of the sample, a detection signal is outputted from a liquid surface detection circuit 151 and accordingly the computer 103 instructs the drive of the movable arm 2 to stop the descending motion. Then, after a specified amount of the sample is sucked into the pipetting probe 105, the pipetting probe 105 ascends up to the upper dead point, the sampling arm 2 swings horizontally to be positioned above the reaction container 106 on a reaction disk 109, and then the sample pipetting probe 105 descends and discharges the previously sucked sample into the reaction container 106. When the reaction container with the sample is moved to a reagent mixing position, a suitable reagent corresponding to the item of analysis is mixed from the reagent pipetting probe 110. In the course of sucking the sample and reagent, the liquid surface of the sample in the sample container 101 and that of the reagent in the reagent bottle 112 are detected. A mixture of the sample and reagent in the reagent container is agitated by an agitator 113. While a train of the reaction containers are in transfer, multiple reaction containers move across the beam from a light source 114 and the absorbance or emission of each mixture is measured by a measuring means, photometer 115.

The absorbance signal is inputted into the computer 103 through an interface 104 via an A/D converter 116 and the concentration of the item of analysis is computed.

The analysis result is either printed out on a printer 117 or displayed on the CRT 118 and, at the same time, stored in memory on a hard disk 122. The reaction container 106 after the measurement is washed at the position of a washing mechanism 119. The pump for washing serves to supply clean water into the reaction container and discharges waste water from the reaction container.

In an embodiment in FIG. 1, the sample disk 102 is equipped with three rows of container holders so that the sample containers 101 can be set in three rows coaxially, and a sample sucking position for the sample pipetting probe 105 is determined on each row.

Next, another embodiment of the present invention which employs a liquid surface detection means of a capacitance detection type is explained, using FIG. 2 to FIG. 6. FIG. 2 is an operation sequence diagram in liquid surface detection; FIG. 3 is a descending motion control chart of a prior art; FIG. 4 is a capacitance measurement of a prior art; FIG. 5 is a descending motion control chart of the present invention; and FIG. 6 is a capacitance measurement of the present invention. Cx in FIG. 4 and FIG. 6 represents the capacitance applied to the probe 105. First, the liquid surface detection of a prior art is explained, using FIG. 2 to FIG. 4. FIG. 2 is a state transition diagram in the cross section of the sample container 101, from the start of descent of the sample pipetting probe 105 from the upper dead point until the liquid surface detection.

The probe 105, having recorded the original capacitance as a reference, starts descending from the upper dead point (A). Since what type of a sample container is placed is unknown and, therefore, the descending distance or the distance to the lower dead point is unknown even if the sample container 101 is in place, the probe 105 is always needed to move as much physical length as the maximum stroke, required theoretically, at high speed within a limited motion time as shown in FIG. 3. That is, the probe 105 must always be ready for liquid surface detection even within a motion stroke where the liquid surface detection is apparently not necessary, and hence the probe motion is apt to be affected by a disturbance noise. Then, the probe 105 continues descending and detects an increase in the capacitance when the tip of the probe 105 contacts the liquid surface, and then the probe 105 ceases to descend. As shown in FIG. 4, however, if the sample container 101 is charged with static electricity, particularly inside, the static electricity is discharged towards the tip of the probe 105, due to its electrostatic collecting effect, at a position (B) several mm above the top of the sample container 101 in FIG. 2. Consequently, a noise due to this discharge may cause a false liquid surface to be detected and the probe 105 may cease to descend. A point of discharge depends upon the level of electric charge and the material of the sample container 101 but in most cases, where a noise big enough to cause such wrong detection is generated, the level of electric charge is high and the discharge is caused near the position (B).

Next, the liquid surface detection of the present invention is explained, using FIG. 2, FIG. 5 and FIG. 6. As explained previously, FIG. 2 is a state transition diagram in the cross section of the sample container 101, from the start of descent of the sample pipetting probe 105 from the upper dead point until the liquid surface detection. The probe 105 starts descending from the upper dead point (A) and halts at a position (B) several mm above the top of the sample container 101 for about several hundred ms. During the descending motion from the upper dead point (A) to near the top of the sample container 101, the probe 105 does not take measurement of the liquid surface detection but only performs a constant descending motion. The descending distance is calculated from the detection result of a sample container height detection unit 150. After a suitable descending distance according to the sample container height and a suitable descending speed calculated in a similar manner are set, the probe 105 descends and then halts. As explained above, no measurement of the liquid surface detection is taken within this motion range. In other words, in the prior art, wrong detection due to an disturbance noise can frequently be caused even at a position where no sample is located and accordingly the liquid surface detection is apparently not necessary. In the present invention, however, since wrong detection cannot be caused at the position, it is possible to further improve the reliability. In the next step where the sample pipetting probe 105 further descends to detect the liquid surface, the probe 105 acquires a reference for the liquid surface detection just before starting to further descend. The further descending distance is calculated necessarily from the descending distance already accomplished and the descending speed is calculated in a similar manner. In order to prevent wrong liquid surface detection and increase the detection accuracy, it is essential to set this speed to a value that allows to secure the maximum noise allowance in detecting the liquid surface and also to limit the dipping depth of the probe 105 into the sample to an allowable range.

Next, further effect of halting the probe at a halt position (B) is explained below.

In the prior art, as explained above, if the sample container 101 is charged with static electricity, the static electricity is discharged towards the tip of the probe 105, due to its electrostatic collecting effect, when the probe 105 descends from the upper dead point (A) and reaches at a position (B) several mm above the top of the sample container 101 in the course of the liquid surface detection. That is to say, while the static discharge from the sample container 101 is caused as a disturbance noise in the course of the liquid surface detection and the noise can be a significant cause of wrong liquid surface detection in the prior art, the electrostatic noise is accelerated to be caused while the liquid surface detection is not valid in the present invention so as to be able to drastically reduce the cause of wrong detection due to the electrostatic noise in the course of the liquid surface detection. Although the above explanation refers to a sample container 101 based on FIG. 2, the above effect can be expected not only with the sample container 101 but with other type of container, such as a test tube, used as a container of specimen as shown in FIG. 7.

To mention concretely the halt position (B) in the constant descending motion, the position at which the pipeting probe stops should be up to 5 mm or preferably about 2 mm above the top of the sample container judging from that this distance is long enough to fully discharge the static electricity of the sample container. If the container is filled fully with sample, a position at 2 mm above the top of the container is meaningful in a sense that the probe scarcely contacts the sample in consideration of the sample up above the rim of the container due to the surface tension.

The halt time of the pipeting probe for acquiring a reference for the liquid surface detection will be 100 ms to 1000 ms, preferably about 500 ms, in view of the sufficient time required for discharging the static electricity. The time required for discharging the static electricity is about 50 ms in average and additional 50 ms are needed to stably measure the reference capacitance, thus a halt time of 100 ms is needed at the minimum. To secure a measurement margin, a longer halt time is preferred. However, since increasing the halt time without limit results in increase of the time required for pipeting, an appropriate maximum halt time is determined by trading off with the time permitted for the measurement. The same halt position and halt time as above-mentioned are preferable not only in case of a sample container 101 but in case of other container such as test tube. Although the descending time depends upon the resolution of the vertical motion of the sampling mechanism 1, about 2,000 pps to 4,000 pps could be a realistic speed, if dared to mention, in case the drive for the vertical motion using a pulse motor has the resolution of about 0.1 mm/p.

Although the above explains particularly about a method for detecting the liquid surface by means of the capacitance measurement, halting the pipeting probe above the container is effective, in view of measuring a reference, not only for a liquid surface detection method by means of the capacitance measurement but for a method by means of measuring a change in the resistance, change in the refraction or reflection of light or ultrasonic wave, and a change in the pressure inside the pipeting probe.

Another embodiment according to the present invention is explained below, using FIG. 7, FIG. 8 and FIG. 9. FIG. 7 is an operation sequence diagram in liquid surface detection; FIG. 8 is a descending motion control chart of the present invention; and FIG. 9 is a capacitance measurement of the present invention. As easily understood from FIG. 7, this embodiment of the present invention is an example where a test tube is used as a sample container. When a test tube 6 is used as a sample container, it is a general practice to install a container holder 8 to hold the top of the test tube 6 as shown in FIG. 7 so as to secure the relative position between the probe 105 and the test tube 6, that is, to prevent the test tube 6 from being fallen down. In a similar manner as in the afore-mentioned embodiment, the probe 105 starts descending from the upper dead point (A) and halts at a position (B) several mm above the test tube 6 for several hundred ms, acquires a reference for the liquid surface detection there, and then descends further for detecting the liquid surface. When the test tube 8 is used as a sample container, it is necessary to set the detectable liquid surface range longer than when the sample container 101 is used in the afore-mentioned embodiment. For this reason, the motion speed between the upper dead point (A) and the position (B) above the top of the test tube must be faster than in the afore-mentioned embodiment so as to secure the time required for the liquid surface detection as shown in FIG. 8, that is, so as to be able to take the liquid surface measurement at a speed as slow as possible.

Then, an effect of halting the probe at a halt position (B) is explained below. When the probe 105 descends and then halts at the halt position (B), the capacitance Cx increases because of the floating capacitance Cf of the container support 8 as shown in FIG. 9. For this reason, if a reference for the liquid surface detection is acquired at the upper dead point (A) as in the prior art, there remains a possibility of wrong detection because of an increase Cf. According to the present invention, however, since a reference is acquired at the halt position (B), the effect of the floating capacitance Cf of the container holder can be eliminated and accordingly stable and accurate detection is possible.

Even when the sample 7 itself is electrically charged after the liquid surface detection or when the probe 105 misses the liquid surface due to the effect of bubbles, a recovery step of descending the probe 105 further from the position and taking the liquid surface measurement again as shown by a dotted line in FIG. 8 and FIG. 9 makes it possible to provide a much more reliable pipeting mechanism. The above further descent can be operated in the same analysis cycle in view of the processing capacity of the analyzer or in the next cycle in view of the pipeting accuracy of the sample. This embodiment does not cover detailed method for judging the necessity of the above recovery cycle, it can be easily realized by, for example, monitoring the detection level in the liquid level detection circuit 151 periodically for several hundred ms after the halt of the probe 105.

As explained above, according to the present invention, optimizing the descending motion control at the time of acquiring a reference in the course of the liquid level detection of the sample in the sample container placed on a sample container holding means and the descending motion control at the time of contacting the liquid surface makes it possible to drastically improve the resistance against static discharge and disturbance noise from the container and also to reduce the dipping depth of the probe in the sample inside the sample container to a suitable level, both regardless of the type of the sample container. As a result, carry-over of the sample can be decreased and contamination between samples can be eliminated.

Figure 1:
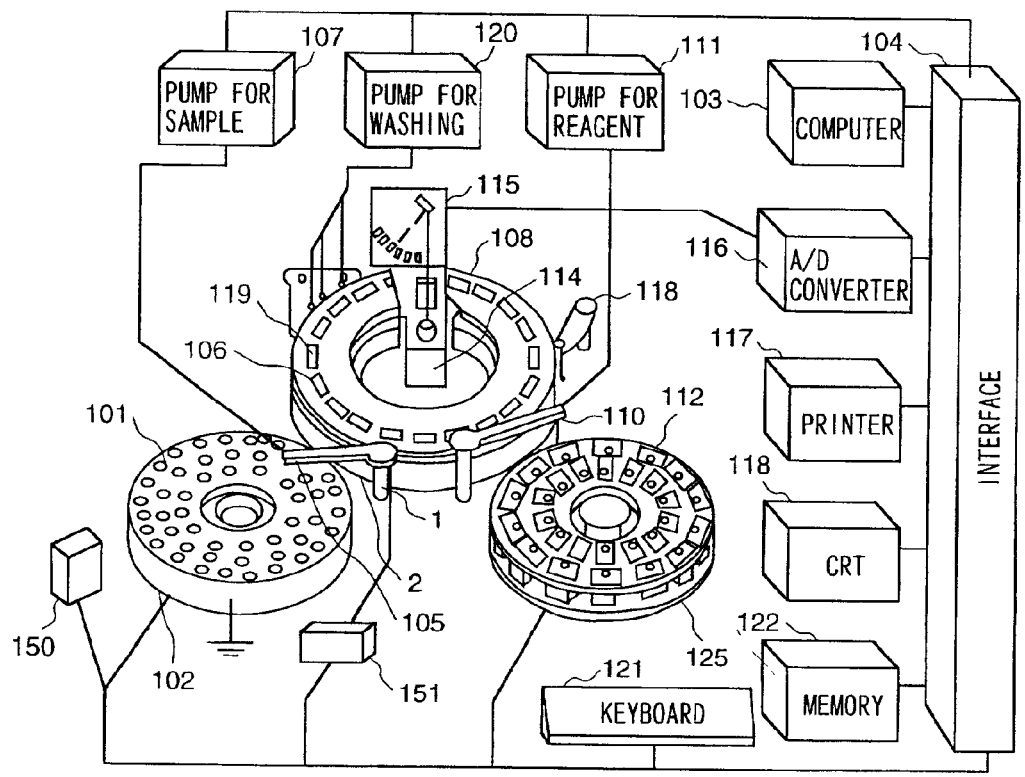
FIG. 1 is a schematic diagram of an automatic analyzer to which the present invention applies.
Figure 2:
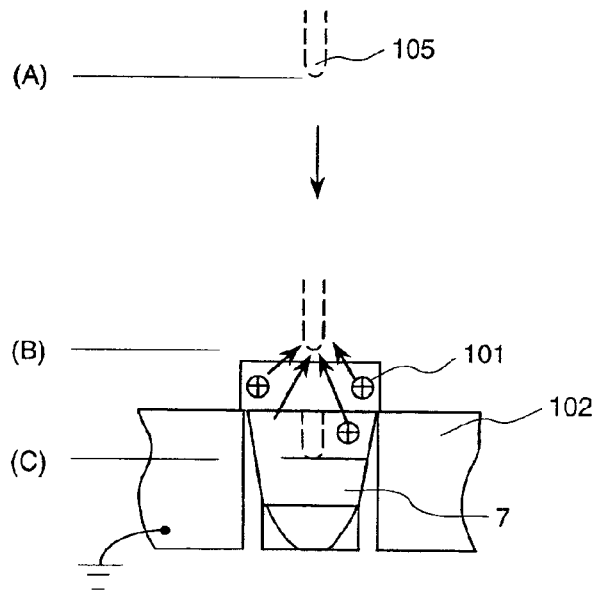
FIG. 2 is an operation sequence diagram in liquid surface detection.
Figure 3:
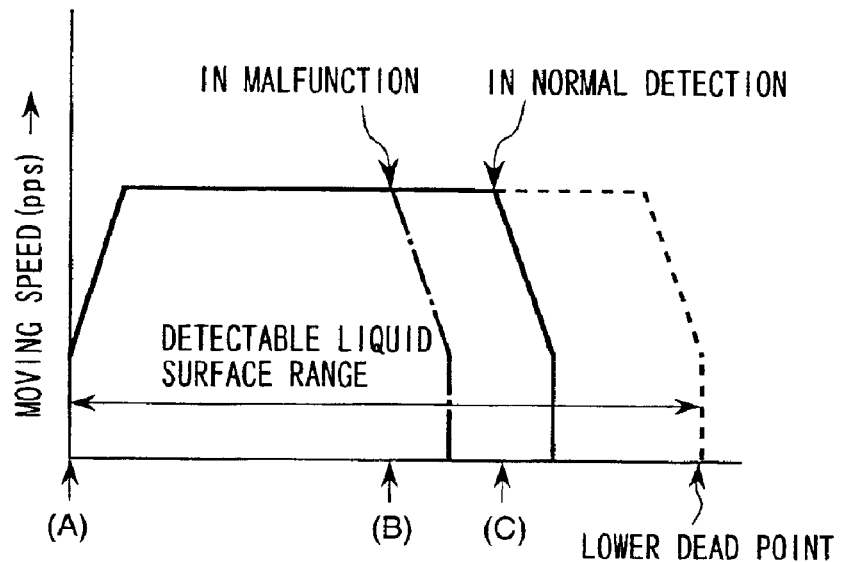
FIG. 3 is a descending motion control chart of a prior art.
Figure 4:
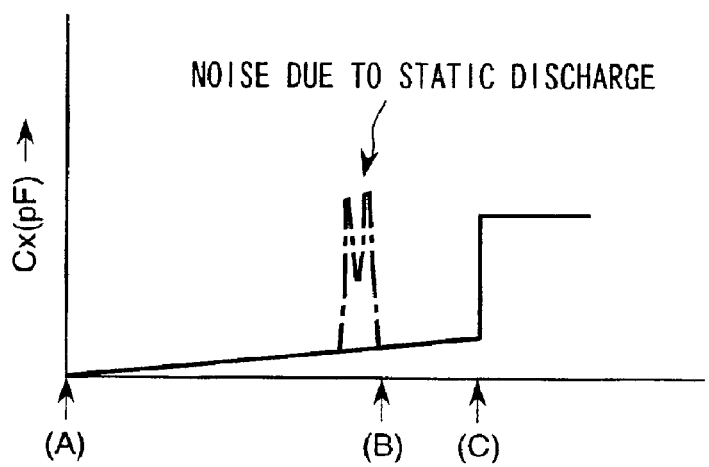
FIG. 4 is a capacitance measurement of a prior art.
Figure 5:
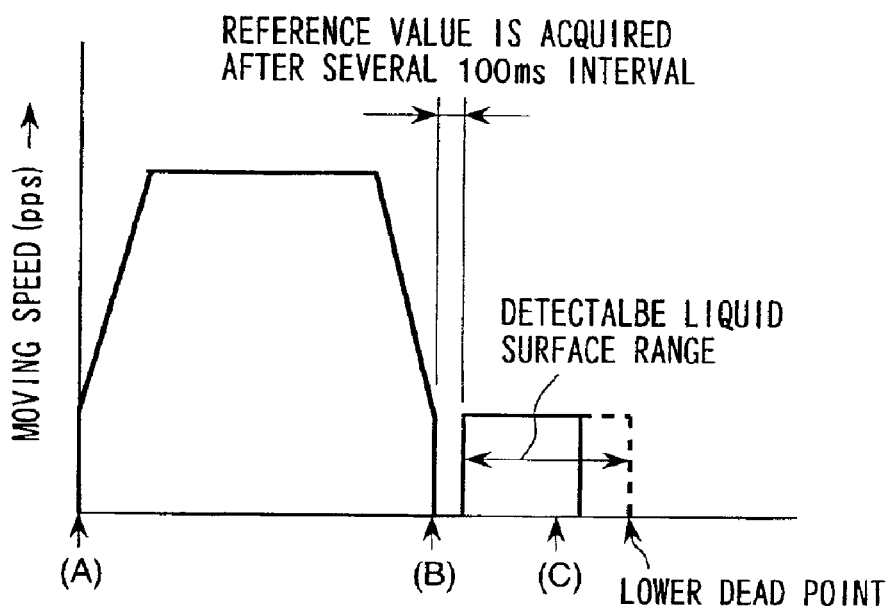
FIG. 5 is a descending motion control chart of the present invention.
Figure 6:
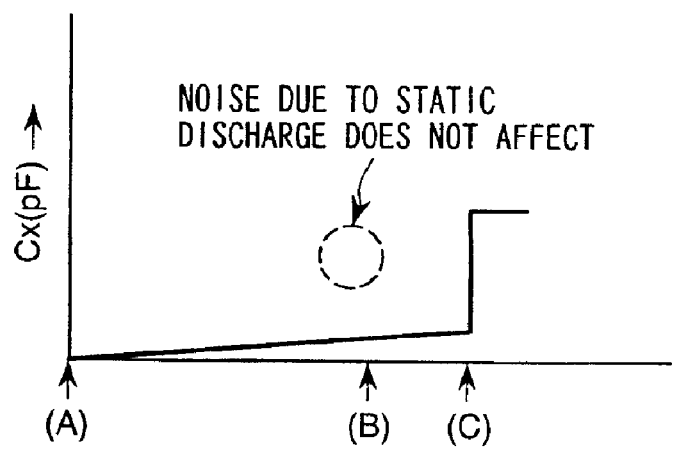
FIG. 6 is a capacitance measurement of the present invention.
Figure 7:
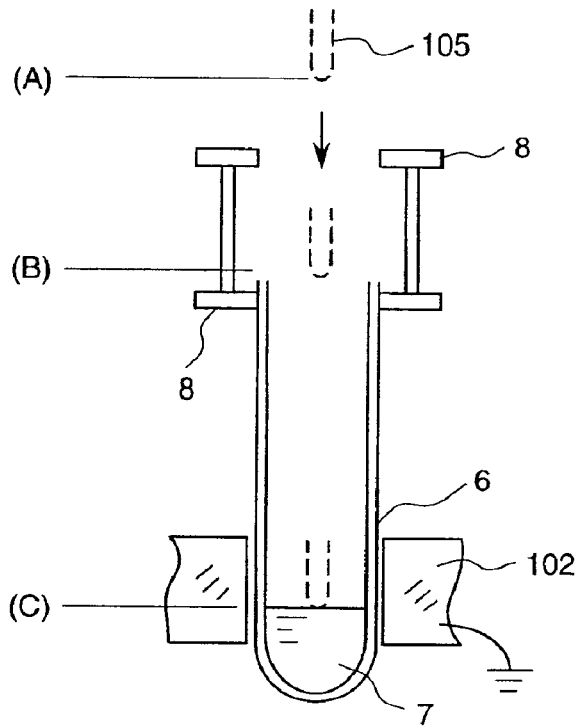
FIG. 7 is an operation sequence diagram in liquid surface detection.
Figure 8:
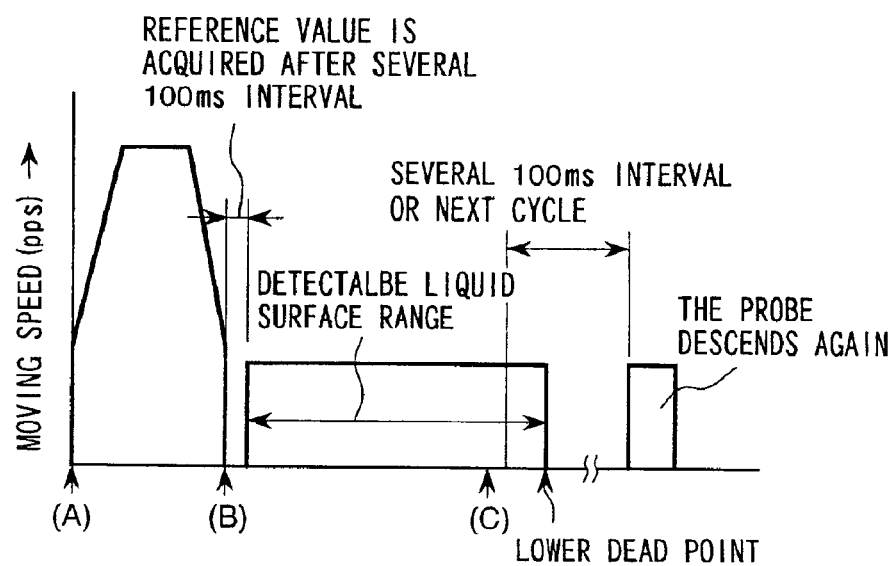
FIG. 8 is a descending motion control chart of the present invention.
Figure 9:
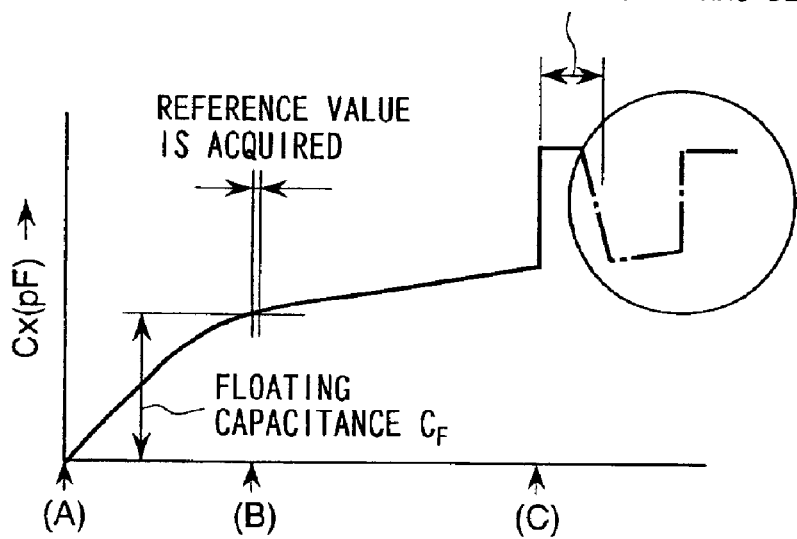
FIG. 9 is a capacitance measurement of the present invention.

What is claimed is:

1. A method for detecting a surface position of liquid of an automatic analyzer comprising, means for moving down a pipetting probe to immerse into said liquid in a first container, means for pipetting liquid from said first container to a second container by said pipetting probe, means for measuring the content of said second container, and electrostatic capacitance measuring means for measuring electrostatic capacitance between said pipetting probe and said liquid in said first container, said method for detecting said surface position comprising the steps of:

stopping said pipetting probe once after moving down said pipetting probe to a position previously set, measuring a standard electrostatic capacitance between said pipetting probe and said liquid in said first container relating to said position previously set, and detecting a surface position of said liquid by comparing said electrostatic capacitance obtained while said pipetting probe is moved down with said standard electrostatic capacitance.

2. An automatic analyzer comprising:

means for moving down a pipetting probe to immerse said pipetting probe into liquid in a first container;

means for pipetting liquid from said first container to a second container by said pipetting probe;

means for measuring the content of said second container;

electrostatic capacitance measuring means for measuring electrostatic capacitance between said pipetting probe and said liquid in said first container; and control means for controlling operation of said pipetting probe, wherein said control means once stops said pipetting probe after moving down said pipetting probe to a position previously set, measures a standard electrostatic capacitance between said pipetting probe and said liquid in said first container relating to said position previously set, detects a surface position of said liquid by comparing said electrostatic capacitance obtained while said pipetting probe is moved down with said standard electrostatic capacitance, and adjusts a distance which said pipetting probe immerses into said liquid in said first container.

3. An automatic analyzer according to claim 2, wherein said electrostatic capacitance between said pipetting probe and said liquid in said first container is started to be measured after said control means once stops said pipetting probe.

4. An automatic analyzer according to claim 2, comprising:

a detecting means for detecting a height of said first container, wherein said position previously set is set based on said height of said first container.

5. An automatic analyzer according to claim 2, wherein said detecting means for detecting a height of said first container judges a kind thereof and shows said height corresponding to said kind previously stored based on said kind detected.

6. An automatic analyzer according to claims 2 to 5, wherein said pipetting probe moves down to said position previously set more quickly than said pipetting probe moves down after temporarily stopping.

* * * * *